(12) United States Patent
Zhu et al.

(10) Patent No.: US 9,791,336 B2
(45) Date of Patent: Oct. 17, 2017

(54) SYSTEM AND METHOD FOR HEAD ACCELERATION MEASUREMENT IN HELMETED ACTIVITIES

(71) Applicant: Evigia Systems, Inc., Ann Arbor, MI (US)

(72) Inventors: Weibin Zhu, Saline, MI (US); Navid Yazdi, Ann Arbor, MI (US)

(*) Notice: Subject to any disclaimer, the term of this patent is extended or adjusted under 35 U.S.C. 154(b) by 376 days.

(21) Appl. No.: 14/621,630

(22) Filed: Feb. 13, 2015

(65) Prior Publication Data

US 2015/0226621 A1    Aug. 13, 2015

Related U.S. Application Data

(60) Provisional application No. 61/965,974, filed on Feb. 13, 2014.

(51) Int. Cl.
*G01L 5/00* (2006.01)
*G06F 19/00* (2011.01)

(52) U.S. Cl.
CPC ........ *G01L 5/0052* (2013.01); *G06F 19/3418* (2013.01); *G06F 19/3481* (2013.01)

(58) Field of Classification Search
CPC . G01L 5/0052; G06F 19/3418; G06F 19/3481
See application file for complete search history.

(56) References Cited

U.S. PATENT DOCUMENTS

| | | | |
|---|---|---|---|
| 4,161,874 A | 7/1979 | Specker | |
| 4,461,553 A | 7/1984 | Doerr | |
| 4,935,748 A | 6/1990 | Schmidt | |
| 5,383,363 A | 1/1995 | Kulmaczewski | |
| 5,621,922 A | 4/1997 | Rush, III | |
| 5,819,206 A | 10/1998 | Horton | |
| 5,978,972 A | 11/1999 | Stewart | |
| 6,563,417 B1 | 5/2003 | Shaw | |
| 6,691,585 B2 | 2/2004 | Ahn | |
| 6,826,509 B2 | 11/2004 | Crisco, III | |
| 6,834,436 B2 | 12/2004 | Townsend | |

(Continued)

FOREIGN PATENT DOCUMENTS

| | | | | |
|---|---|---|---|---|
| CA | 2922191 A1 * | 2/2015 | ............. | A42B 3/046 |
| WO | WO 2015026962 A1 * | 2/2015 | ............. | A42B 3/046 |

OTHER PUBLICATIONS

A. J. Padgaonkar, K. W. Krieger and A. I. King, "Measurement of Angular Acceleration of a Rigid Body Using Linear Accelerometers," J. Appl. Mech. 42(3), 552-556 Sep. 1, 1975, doi:10.1115/1.3423640.

(Continued)

*Primary Examiner* — Laura Menz
(74) *Attorney, Agent, or Firm* — James M. Smedley LLC; James Michael Smedley, Esq.

(57) ABSTRACT

The present invention generally relates to a system and method for the precise measurement of acceleration, movement, and other forces imparted on a body or object. Specifically, the invention relates to a system and method for measuring head accelerations in helmeted activities including, but not limited to, football, ice hockey, and lacrosse. Certain embodiments of the invention may include a wireless link to a remote recording station with near real-time data analysis and reporting of force and kinetics measured by the system.

18 Claims, 8 Drawing Sheets

(56) References Cited

U.S. PATENT DOCUMENTS

| | | | |
|---|---|---|---|
| 7,204,165 | B1 | 4/2007 | Plaga |
| 9,305,441 | B1* | 4/2016 | Cronin .................. G08B 7/06 |
| 2011/0060260 | A1* | 3/2011 | Siegler ................ A42B 3/0473 |
| | | | 602/18 |
| 2012/0210498 | A1* | 8/2012 | Mack .................. A42B 3/0466 |
| | | | 2/414 |
| 2012/0223833 | A1* | 9/2012 | Thomas .............. G06F 19/3418 |
| | | | 340/539.12 |
| 2012/0297525 | A1* | 11/2012 | Bain ...................... A42B 3/069 |
| | | | 2/411 |
| 2013/0192336 | A1* | 8/2013 | O'Connor .......... A41D 13/0506 |
| | | | 73/12.01 |
| 2014/0247206 | A1* | 9/2014 | Grokop ................ G06F 1/3287 |
| | | | 345/156 |
| 2014/0323921 | A1* | 10/2014 | Huang .................. A61B 5/4064 |
| | | | 600/587 |
| 2015/0077246 | A1* | 3/2015 | Eppler, Jr. ............. A42B 3/046 |
| | | | 340/539.12 |
| 2015/0080766 | A1* | 3/2015 | Ji ............................ A61B 5/11 |
| | | | 600/595 |
| 2015/0080768 | A1* | 3/2015 | Huang ................ A42B 3/0473 |
| | | | 600/595 |
| 2015/0100141 | A1* | 4/2015 | Hughes ................ A61B 5/1118 |
| | | | 700/92 |
| 2015/0226621 | A1* | 8/2015 | Zhu ...................... G01L 5/0052 |
| | | | 702/41 |
| 2016/0157543 | A1* | 6/2016 | Huang ................ A42B 3/0473 |
| | | | 2/411 |
| 2016/0213299 | A1* | 7/2016 | Allen .................... A61B 5/4064 |
| 2016/0213300 | A1* | 7/2016 | Allen .................... A61B 5/4064 |
| 2016/0220167 | A1* | 8/2016 | Allen .................... A61B 5/4064 |
| 2016/0262694 | A1* | 9/2016 | Calcano ..................... A61L 2/16 |
| 2016/0321425 | A1* | 11/2016 | Ji ........................ G06F 19/3437 |
| 2017/0020205 | A1* | 1/2017 | Eppler, Jr. ............. A42B 3/046 |
| 2017/0111722 | A1* | 4/2017 | Forstner .................. G06F 3/162 |
| 2017/0181712 | A1* | 6/2017 | John ..................... A61B 5/7275 |
| 2017/0215011 | A1* | 7/2017 | Goldstein ............ H04R 25/305 |

OTHER PUBLICATIONS

Yun-Seok Kang, Kevin Moorhouse and John H. Bolte, "Measurement of Six Degrees of Freedom Head Kinematics in Impact Conditions Employing Six Accelerometers and Three Angular Rate Sensors (6aω Configuration),"J Biomech Eng 133(11), 111007 Dec. 8, 2011, doi:10.1115/1.4005427.

Shea RT1, Viano DC, "Computing body segment trajectories in the Hybrid III dummy using linear accelerometer data," J Biomech Eng. Feb. 1994;116(1):37-43.

E. Takhounts, R. Eppinger, R. Tannous,J. Q. Campbell, E. Power, L. Shook, and V. Hasija, "Analysis of 3D Rigid Body Motion Using the Nine accelerometer Array System," Proceedings of the Thirty-First International Workshop, 2003.

Joseph J. Crisco, Jeffrey J. Chu, Richard M. Greenwald, "An Algorithm for Estimating Acceleration Magnitude and Impact Location Using Multiple Non Orthogonal Single-Axis Accelerometers," J Biomech Eng. Dec. 2004;126 (6):849-54.

Namik Ciblak,"Determining the Angular Motion of a Rigid Body Using Linear Accelerometers Without Integration," Recent Advances in Space Technologies, 2007. RAST '07. 3rd International Conference on,pp. 585-590, Jun. 14-16, 2007.

CDC, "Traumatic Brain Injury in US, Emergency Department Visits, Hospitalizations and Deaths 2002-2006," Mar. 2010,www.cdc.gov/TraumaticBrainInjury.

J.Gilchrist et. al, "Nonfatal sports and recreation related traumatic brain injuries among children and adolescents treated in emergency departments in the United States, 2001-2009", MMWR 2011: 60(39);1337-1342.

LM. Gessel et. al. "Concussions Among United States High School and Collegiate Athletes".J Athl Train. 2007; 42(4):495-503.

A. I. King, et. al "Is Head Injury Caused by Linear or Angular Acceleration?," Proc.of the International Research Conference on the Biomechanics of Impacts (IRCOBI), Lisbon, Portugal., 2003.

R. Greenwald, et. al, "Head Impact Severity Measures for Evaluating Mild Traumatic Brain Injury Risk Exposure," Neurosurgery, 62(4), 2008, pp. 789-798.

S. Rowson, G. Brolinson, M. Goforth, D. Dietter, S. Duma, "Linear and Angular Head Acceleration Measurements in Collegiate Football," J. of Biomechanics Engineering, Jun. 2009, vol. 131.

S.E. Olvey, T. Knox, K.A. Cohn, "The Development of a Method to Measure Head Acceleration and Motion in High-Impace Crashes", Neurosurgery, Mar. 2004, 54 (3) 672-677.

T. Knox, "Validation of Earplug Accelerometers as a Means of Measuring Head Motion", SAE Paper 2004-01-3538, Proc. SAE Motorsports Conf. (P-392) 2004.

N. Yazdi, T. Knox, J. Plaga, Y. Zhang, R. Hower,"Wireless Acceleration and Impact Recording Chips", SAE International Journal of Passenger Cars-Electronic and Electrical Systems, 1(1): 664-669, Apr. 2009.

.N. Yazdi, A.Ayazi, and K.Najafi, "Micromachined Inertial Sensors", Proceedings of the IEEE,, vol. 86, No. 8, pp. 1640-1659, Aug. 1998.

Hill, Doug, Knox, Ted, Crockett, Dave. Monitoring Race Car Drivers Using Helmet and Head-Mounted Sensors. SAE Technical Papers 2000-01-3557. Presented at the SAE Motorsports Engineering Conference & Exposition, Dearborn, Michigan, Nov. 13-16, 2000.

Knox, Ted, (2002) Use of Instrumented Earplugs to Measure Driver Head Accelerations, SAE paper 02MEC-29 presented at the 2002 SAE Motorsports Exhibition and Conference, Dec. 2002 in Indianapolis, IN.

* cited by examiner

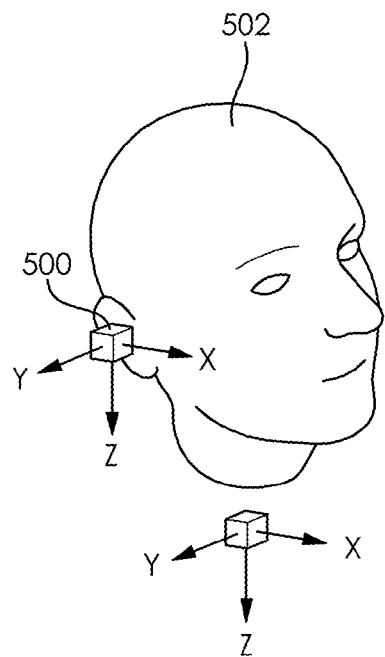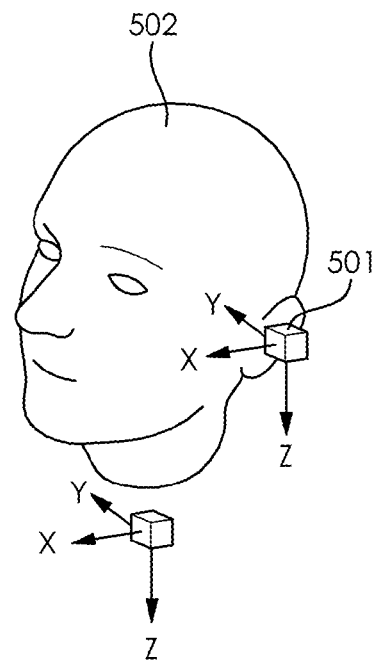
FIG. 5A        FIG. 5B
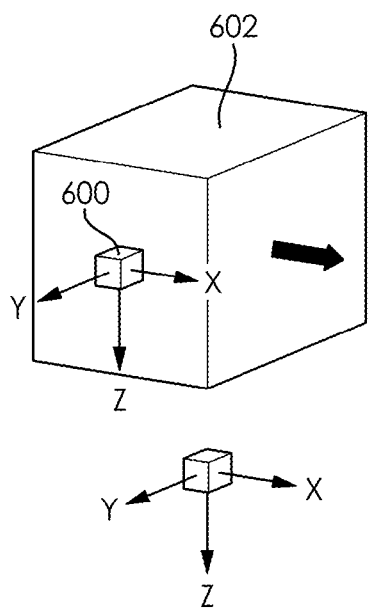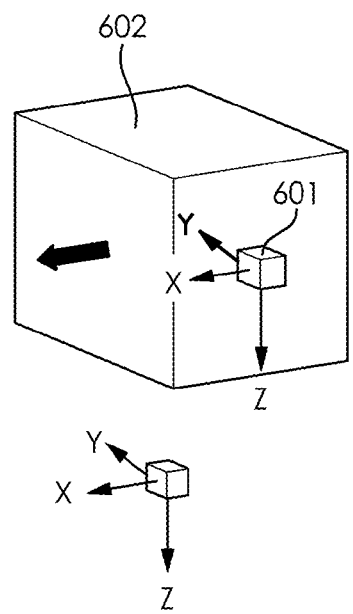
FIG. 6A        FIG. 6B

SYSTEM AND METHOD FOR HEAD ACCELERATION MEASUREMENT IN HELMETED ACTIVITIES

FIELD OF THE INVENTION

The present invention generally relates to a system and method for the precise measurement of acceleration, movement, and other forces imparted on a body or object. Specifically, the invention relates to a system and method for measuring head accelerations in helmeted activities including, but not limited to, football, ice hockey, and lacrosse. Certain embodiments of the invention may include a wireless link to a remote recording station with near real-time data analysis and reporting of force and kinetics measured by the system.

CROSS-REFERENCE TO RELATED APPLICATIONS

This application claims the benefit of U.S. Provisional Patent Application No. 61/965,974, filed on Feb. 13, 2014, which is hereby incorporated by reference in its entirety.

BACKGROUND OF THE INVENTION

The US Center for Disease Control and Prevention (CDC) reports that ~1.7 million people sustain traumatic brain injury (TBI) each year. With the increased knowledge of the possible serious and long lasting ramifications of TBI, a great deal of research has become focused on developing improved protective gear and procedures to help protect against the injuries induced by TBI and mild-TBI, especially in sports and military applications. Due to the limitation of in-vivo strain measurement in human brain, other kinematic parameters of head, such as head linear acceleration (to define linear impact of head contact) and angular acceleration (to define inertial loading of head), are used for study of brain injury mechanisms. Several systems incorporating microelectromechanical systems (MEMS) inertial sensors into helmets have been developed and employed, with the Head Impact Telemetry System (HITS) being one of the earliest and most widely used.

The primary disadvantage of using sensors that are incorporated into a helmet is that the sensors in the helmet may not accurately measure the acceleration forces being delivered to the head of the user. In particular, the head acceleration induced by an impact could be different from the helmet acceleration depending on variations caused by different fit tightness and wear conditions between the head of the user and the helmet. For more precise measurements of head accelerations, it is necessary to have any sensors coupled more directly to the head of a user to eliminate the inaccuracies caused by the fit of a helmet and the helmet movements that are independent of the head of the user. While certain head acceleration sensors in the form of earplugs have been developed, those sensors require a hard wired connection to the data recording portion of the system.

Therefore, there is a need in the art for a system and method for wirelessly measuring and recording head acceleration caused by impacts in helmeted activities through the use of a reduced number sensors that are tightly coupled to the head of a user. These and other features and advantages of the present invention will be explained and will become obvious to one skilled in the art through the summary of the invention that follows.

SUMMARY OF THE INVENTION

Accordingly, embodiments of the present invention are directed to (i) a wireless head acceleration recording system that monitors head acceleration via two or more sensors that are tightly coupled to the head and communicate through a short range wireless link to in-helmet recorder electronics and (ii) a method for calculating head acceleration based on data received an inertial sensor set. In a preferred embodiment, the sensors may be embedded in commonly used articles such as earplugs and mouth guards in order to provide a better comfort and fit for a user. Some embodiments of the present invention may include an in-helmet recorder unit that is capable of transmitting the gathered sensor data to a remote recording station via a longer range wireless link.

According to an embodiment of the present invention, a system for determining the acceleration delivered to an object as a result of an impact, the system comprising: an acceleration data processing module comprising computer-executable code stored in non-volatile memory, a processor, a memory, and a communications means, wherein the acceleration data processing module, the processor, the memory, and the communications means are operably connected and are configured to: detect an acceleration force being applied to a rigid body with a plurality of inertial sensor sets comprising at least a first set of inertial sensors that is attached to the rigid body at a first reference point and a second set of inertial sensors that is attached to the rigid body at a second reference point such that the second reference point is aligned on a common axis with the first reference point, wherein an origin reference point exists on the common axis substantially equidistant from the from the first and the second reference points, collect acceleration data using the inertial sensor sets, wherein the acceleration data is measured at least at the first and second reference points, transmit the acceleration data to the acceleration data processing module for analysis, and analyze the acceleration data collected by the inertial sensor sets, wherein the acceleration data is used to calculate origin point kinematics.

According to an embodiment of the present invention, the rigid body has a center of gravity with center of gravity kinematics and the acceleration data processing module, the processor, the memory, and the communications means are operably connected and further configured to calculate the center of gravity kinematics from the origin point kinematics based on a geometrical relationship between the center of gravity and the origin reference point.

According to an embodiment of the present invention, the acceleration data processing module, the processor, the memory, and the communications means are operably connected and are configured to: identify when the acceleration value for the center of gravity of the rigid body exceeds a preset threshold and send an alert notification when said acceleration value for said center of gravity of said rigid body exceeds said preset threshold.

According to an embodiment of the present invention, the first set of inertial sensors consists of three orthogonal axes linear accelerometers and the second set of inertial sensors consists of three orthogonal linear accelerometers and a single-axis gyroscope with a sensing axis that is in parallel with the common axis existing between the first and second reference points.

According to an embodiment of the present invention, the plurality of inertial sensor sets is further comprised of a third set of inertial sensors that is attached to the rigid body at a third reference point such that the third reference point is aligned with the origin reference point on a secondary axis that is perpendicular to the common axis thereby enabling the third set of inertial sensors to collect the acceleration data at the third reference point for use in calculating the origin point kinematics.

According to an embodiment of the present invention, the acceleration data processing module, the processor, and the memory are configured as a remote recording station.

According to an embodiment of the present invention, the system is further comprised of a wireless data link unit, wherein the wireless data link unit, the acceleration data processing module, the processor, the non-transitory computer readable memory, and the communications means are operably connected and are configured to: receive the acceleration data from the plurality of inertial sensor sets and transmit the acceleration data to the remote recording station.

According to an embodiment of the present invention, the wireless data link unit is attached to a helmet.

According to an embodiment of the present invention, the acceleration data processing module, the processor, the memory, and the communications means are operably connected and are configured to: identify when the acceleration value for the origin reference point of the rigid body exceeds a preset threshold and send an alert notification when the acceleration value for the origin reference point of the rigid body exceeds the preset threshold.

According to an embodiment of the present invention, the acceleration data processing module, the processor, the memory, and the communications means are operably connected and are configured to: receive acceleration data of a secondary body, compare the acceleration data of the secondary body to the acceleration data of the rigid body, and correct an acceleration value of the secondary body for a lack of tight coupling with the rigid body.

According to an embodiment of the present invention, the origin point kinematics are calculated in six-degrees of freedom.

According to an embodiment of the present invention, the rigid body is a head of a person.

According to an embodiment of the present invention, one or more inertial sensor sets in the plurality of inertial sensor sets is formed as an earpiece.

According to an embodiment of the present invention, one or more inertial sensor sets in the plurality of inertial sensor sets is formed as a mouth guard.

According to an embodiment of the present invention, a method for determining the acceleration delivered to an object as a result of an impact force, the method comprising the steps of: detecting an acceleration force being applied to a rigid body with a plurality of inertial sensor sets comprising at least a first set of inertial sensors that is attached to the rigid body at a first reference point and a second set of inertial sensors that is attached to the rigid body at a second reference point such that the second reference point is aligned on a common axis with the first reference point, wherein an origin reference point exists on the common axis substantially equidistant from the from the first and the second reference points, collecting acceleration data using the inertial sensor sets, wherein the acceleration data is measured at least at the first and second reference points, transmitting the acceleration data to the acceleration data processing module for analysis, and analyzing the acceleration data collected by the inertial sensor sets, wherein the acceleration data is used to calculate origin point kinematics.

According to an embodiment of the present invention, the rigid body has a center of gravity with center of gravity kinematics and further comprising the step of calculating the center of gravity kinematics from the origin point kinematics based on a geometrical relationship between the center of gravity and the origin reference point According to an embodiment of the present invention, the method further comprises the step of: identifying when the acceleration value for the center of gravity of the rigid body exceeds a preset threshold and sending an alert notification when the acceleration value for the center of gravity of the rigid body exceeds the preset threshold.

According to an embodiment of the present invention, the method further comprises the step of detecting an acceleration force with a third set of inertial sensors that is attached to the rigid body at a third reference point such that the third reference point is aligned with the origin reference point on a secondary axis that is perpendicular to the common axis thereby enabling the third set of inertial sensors to collect the acceleration data at the third reference point for use in calculating the origin point kinematics.

According to an embodiment of the present invention, the method further comprises the steps of: receiving the acceleration data from the plurality of inertial sensor sets and transmitting the acceleration data to the remote recording station.

According to an embodiment of the present invention, the method further comprises the steps of: identifying when the acceleration value for the origin reference point of the rigid body exceeds a preset threshold and sending an alert notification when the acceleration value for the origin reference point of the rigid body exceeds the preset threshold.

According to an embodiment of the present invention, the method further comprises the steps of: receiving acceleration data of a secondary body, comparing the acceleration data of the secondary body to the acceleration data of the rigid body, and correcting an acceleration value of the secondary body for a lack of tight coupling with the rigid body.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

BRIEF DESCRIPTION OF THE DRAWINGS

FIG. 5A is a right side view of a coordinate system for a two inertial sensor system attached to a head in accordance with an embodiment of the present invention;

FIG. 5B is a left side view of a coordinate system for a two inertial sensor system attached to a head in accordance with an embodiment of the present invention;

FIG. 6A is a right side view of a coordinate system for a two inertial sensor system attached to a rigid body in accordance with an embodiment of the present invention;

FIG. 6B is a left side view of a coordinate system for a two inertial sensor system attached to a rigid body in accordance with an embodiment of the present invention;

DETAILED SPECIFICATION

The present invention generally relates to a system and method for the precise measurement of acceleration, movement, and other forces imparted on a body or object. Specifically, the invention relates to a system and method for measuring head accelerations in helmeted activities including, but not limited to, football, ice hockey, and lacrosse. Certain embodiments of the invention may include a wireless link to a remote recording station with near real-time data analysis and reporting of force and kinetics measured by the system.

According to an embodiment of the present invention, the system may be comprised of a plurality of inertial sensors that include, but are not limited to, accelerometers and gyroscopes. In a preferred embodiment, the plurality of inertial sensors may be organized into groups of inertial sensors sets, each of which is a cohesive unit capable of measuring kinematic data such as acceleration and, or velocity. In the preferred embodiment, one or more inertial sensor sets are attached to the head of person or the helmet that person is wearing so as to measure the head acceleration experienced by that person as the result of an impact force on the head or body. In an alternate preferred embodiment, the one or more inertial sensor sets could be appropriately aligned on any rigid body that a person desires to measure. One of ordinary skill in the art would appreciate that each inertial sensor set could include any suitable number of inertial sensors, and embodiments of the present invention are contemplated for use with any such number of inertial sensors.

Figure 12:
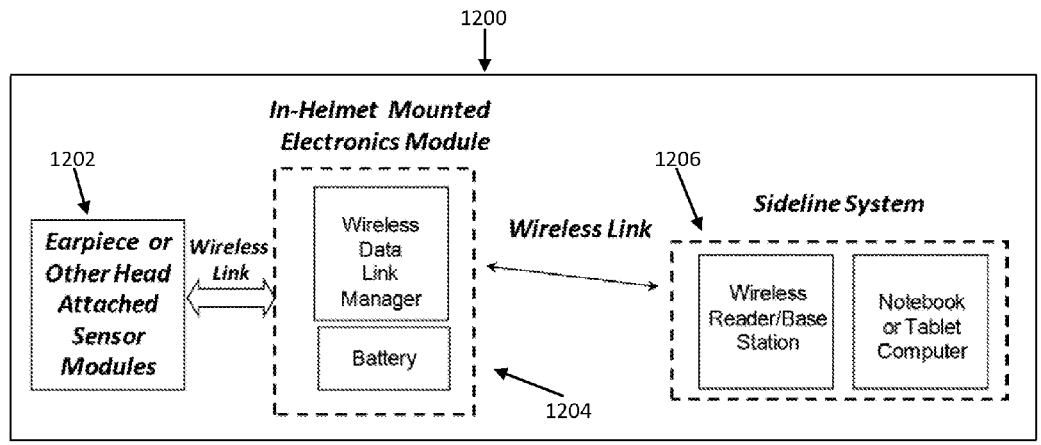
FIG. 12 illustrates a schematic overview of a head acceleration measurement system that only uses head attached inertial sensors in accordance with an embodiment of the present invention.
Figure 13:
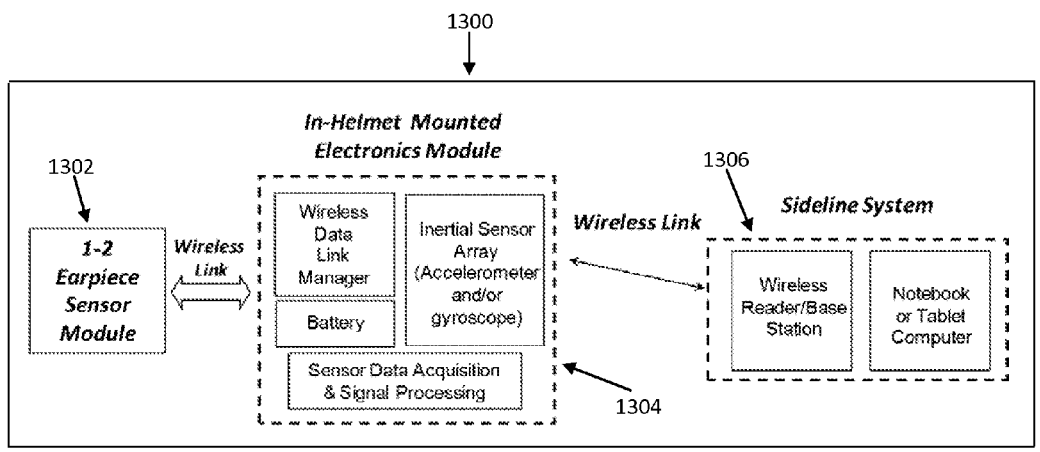
FIG. 13 illustrates a schematic overview of a head acceleration measurement system that uses both head and helmet mounted inertial sensors in accordance with an embodiment of the present invention.
Figure 14:
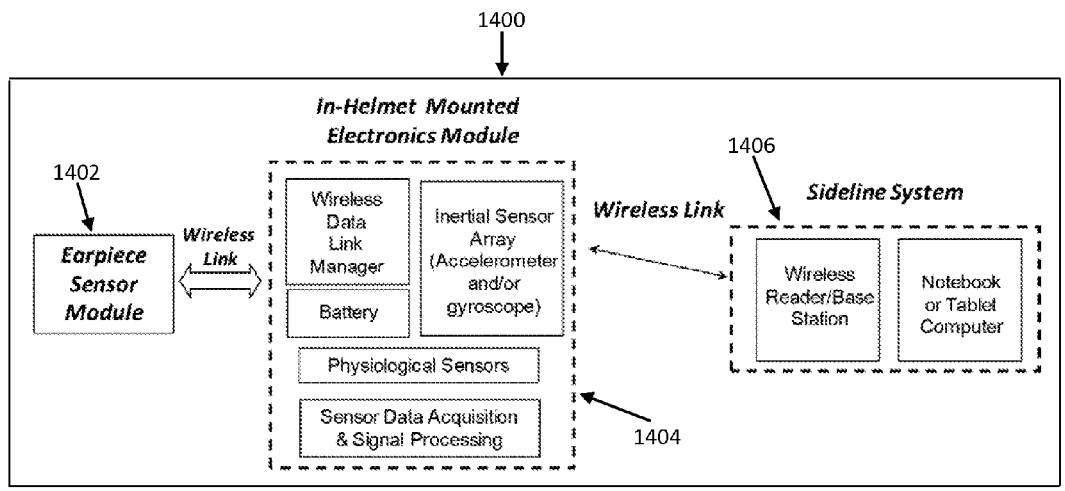
FIG. 14 illustrates a schematic overview of a head acceleration measurement system that uses both head and helmet mounted inertial sensors, as well as other physiological sensors in accordance with an embodiment of the present invention.

According to a preferred embodiment, the system employs inertial sensors that are embedded in earpieces. Embedding sensors in earpieces effectively attaches the inertial sensors directly to the head, thereby allowing the sensors to more accurately measure the movement of the head itself, as opposed to movement of a helmet that is worn over the head. In embodiments where the inertial sensor is embedded in an earpiece, the sensor is molded within silicone or other similar plug material that is comfortable to wear. In some embodiments, the helmet of the person wearing the inertial sensors may provide further mechanical support for the molded earpiece. While the preferred embodiment uses sensors embedded in an earpiece, other schemes for tightly coupling the inertial sensors to the head of person include the use of sensors embedded in a mouth guard or a sensor placed on the teeth, chin, or forehead. One of ordinary skill in the art would appreciate that there are many suitable ways to tightly couple a sensor to the head of a user including, but not limited to, by incorporating a sensor into a wearable article that could be tightly coupled to the head or directly attaching the sensor to some portion of the head, and embodiments of the present invention are contemplated for use when any suitable direct coupling method According to a preferred embodiment of the present invention, the system may be configured to accurately measure and derive six degree-of-freedom head acceleration, movement and kinematics. In the preferred embodiment, sensor data could ultimately be wirelessly transmitted to a remote recording station such as a sideline system in a sports activity or directly to computing device such as a computer, mobile phone or other handheld computing and communication device. The sideline system may consist of a wireless receiver and computing device that processes data in real-time and provides alerts, impact statistics and history per player, and other data visualization. As an illustrative example, FIG. 12 shows a schematic overview of the overall system of one preferred embodiment. In the preferred embodiment, a helmet is configured with a wireless data link unit that is mounted on the helmet and manages electronics for both the link to the inertial sensors connected to the head of a user, as well as the link to the remote recording station. In particular, the wireless data link unit facilitates communication between the inertial sensors connected to the head of a user and the remote recording station. As shown in FIGS. 13 and 14, the wireless data link unit may also be configured with a power source (for example a battery), a data link manger, and sensor signal acquisition and processing components. One of ordinary skill in the art would appreciate that there are numerous tasks that could be controlled by the wireless data link unit, and embodiments of the present invention are contemplated for facilitating any such task.

According to an embodiment of the present invention, the wireless data link unit may support a variety of wireless communication protocols to establish a connection with the inertial and other sensors utilized by the system. In a preferred embodiment, the wireless link between the wireless data link unit in the helmet and the inertial and other sensors connected to the head of a user could be short range employing a near-field inductive coupling, to enable both a data and power link operating on Low Frequency (LF) or High Frequency (HF) bands. For example, the wireless data link unit could be configured to transfer power to the earpiece sensors to support battery-free operation. Alternatively, such a connection could support charging of the internal battery of the earpiece sensor. In the preferred embodiment, the short range wireless link is similar to a radio frequency identification device (RFID) communication on LF or HF bands. In particular, electronics and standard communication protocols employed in RFID systems could be also used in this application. Furthermore, an ultra-high frequency (UHF) RFID could be used in this system. In the preferred embodiment, there is a two-way a wireless communication link between the wireless data link unit and the earpiece sensor to facilitate both receiving data from the earpiece sensor(s) and transferring commands and configuration to the earpiece sensor(s). In an alternate preferred embodiment, there may only be a one-way wireless communication link between the wireless data link unit and the earpiece sensor to facilitate the receipt of data that is measured by the earpiece sensor(s).

Figure 15:
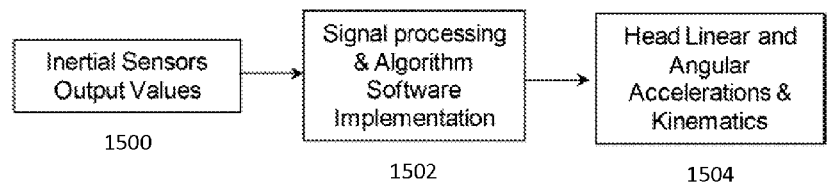
FIG. 15 is a flowchart of an exemplary method of calculating acceleration and kinematic data based on one or more inertial sensors.
Figure 16:
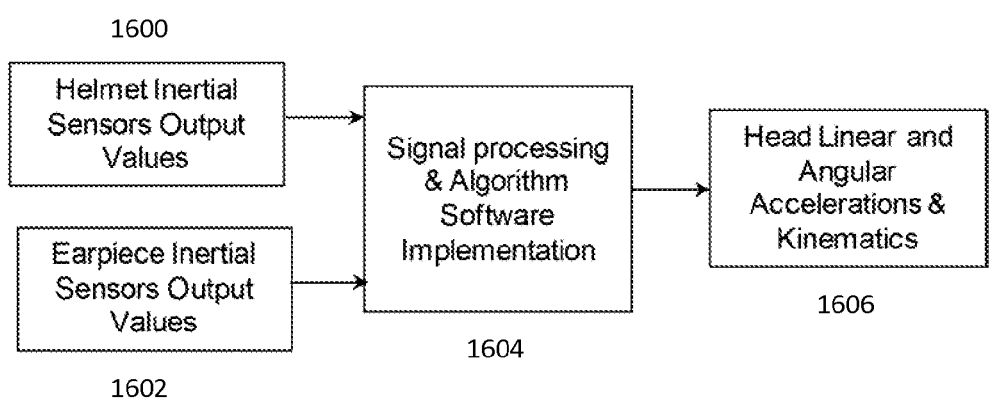
FIG. 16 is a flowchart of an exemplary method of calculating acceleration and kinematic data based on data received on one or more inertial sensors from two separate sources.

Turning now to FIG. 15, an exemplary process of the inertial sensor data flow that uses signal processing and algorithm computation implemented, preferably in software executed on a data processing module using a processor, to derive head 6-DOF motion acceleration and kinematics. In a first preferred embodiment, the inertial sensor data may be collected by sensors attached directly to the body of a person, most notably earpiece sensor(s) as the primary source of data. As an alternate preferred embodiment, FIG. 16 shows an exemplary process of the data flow in the case that the earpiece sensor inertial output are only used as means to compensate for imperfections in the coupling between the helmet and head of a user, where inertial sensors in the helmet are considered to be the primary inertial sensors.

According to a preferred embodiment of the present invention, when the system detects an impact or acceleration impact above a preset threshold, the system will automatically record the acceleration and impact data. Additionally, the detection of an impact or acceleration over a predefined threshold could be useful in identifying and treating possible injuries that the person might suffer as a result of an impact. For example, if an impact or acceleration threshold is exceeded, then the system could alert an appropriate person to perform an examination of the person that experienced the impact. In some embodiments, the system will also transmit the acceleration and impact data to the remote recording station, thereby allowing both a recording and an alerting feature. In a preferred embodiment, the remote recording station may be a laptop computer, tablet, mobile device, smart phone, or similar portable computing device, while in other embodiments that remote recording station is stand-alone data recording and processing unit to which a standard computing device can connect. In some embodiments, the remote recording station may be configured with a user interface, as well as data reporting and alert messaging software. The alerts messaging software could be used to display or send mobile messages including, but not limited to text, push messages, and email to other devices. In a preferred embodiment, the majority of the data processing and calculation processes will be accomplished on the remote recording station. In the preferred embodiment, the remote recording station will perform the most intensive data processing tasks, including, but not limited to the 6-DOF inertial sensor kinematics, as well as other sensor data signal processing, derivation and possibly multiple-sensor data fusion using software embodying an algorithm similar to the one discussed below. In some embodiments, certain data processing and calculation processes may be performed on board the inertial sensors. The data processing tasks that could be accomplished on board the inertial sensor include, but are not limited to, preliminary calculations, data integration, filtering, and compression. One of ordinary skill in the art would appreciate that there are numerous suitable methods for dividing up computing and calculating processes and embodiments of the present invention are contemplated for use with any such division of computing and calculating processes.

According to an embodiment of the present invention as shown in FIGS. 13 and 14, one or more inertial sensors may be mounted in a helmet. In some embodiments, the helmet mounted inertial sensors may be the primary source of acceleration information. In embodiments where the primary inertial sensors are mounted in the helmet, it may be useful for the system to use acceleration data from inertial sensors that are attached directly to the head, for example as a mouth guard or earpiece(s) configured with an inertial sensor. The sensors that are attached directly to the head can be used to correct for any errors caused by a lack of perfect coupling between the head and helmet, as the helmet may, to some degree, move independently of the head. In the preferred embodiment, essentially all or a subset of the available helmet inertial sensor data and head attached inertial sensor data will be compared real-time to derive a transfer function or other models representing the coupling between the head and helmet, and the correction schemes that should be employed to make the output of the helmet sensors a more accurate representation of the actual head accelerations. In a preferred embodiment, the transfer function could be done for each impact (or a subset of impacts) and applied in real-time. In an alternate preferred embodiment, the transfer function could be done offline, whereby the impact data is recorded and evaluated at a later time when the person is done wearing the helmet. In some embodiments, as shown in FIG. 14, the system may be expanded to include other physiological sensors including, but not limited to, heart rate monitors, EEG, and thermometers. In some embodiments, the physiological sensors might be incorporated into the helmet, while in others the physiological sensors might be incorporated into the earpiece or mouth guards along with the inertial sensor modules. One of ordinary skill in the art would appreciate that there are numerous possible sensors and sensor arrangements that could be employed by the system, and embodiments of the present invention are contemplated for use with any such sensor or sensor arrangement.

Figure 10:
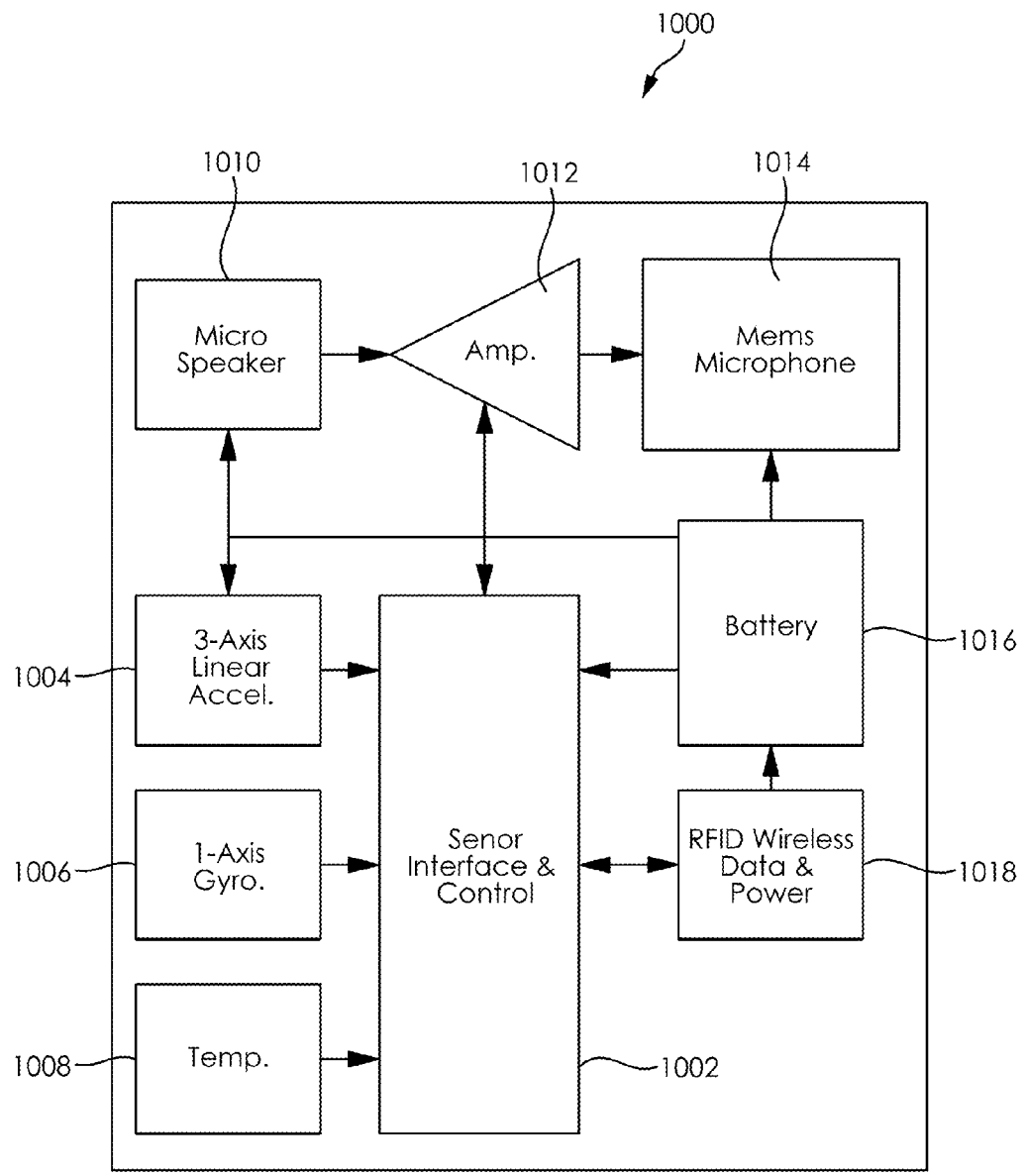
FIG. 10 is a schematic of an exemplary embodiment of an inertial sensor formed as wireless earpiece sensor in accordance with an embodiment of the present invention.

According to an embodiment of the present invention, the head attached sensors may be the primary source of head acceleration and impact data. In a preferred embodiment, inertial sensors may be embedded into an earpiece, mouth guard, or other wearable article that a person could wear on, in, or around the head. As an illustrative example, FIG. 10 shows the schematic of an exemplary earpiece sensor module that could be used to provide both 3-axis linear and 3-axis rotation kinematics and angular acceleration. In some embodiments the sensor module may also include a temperature sensor. Data from the earpiece sensor or similar head connected sensor may be incorporated in the system for real-time data streaming to a remote recording station for analysis and reporting. In some embodiments, as shown in FIG. 10, the sensor may also include an embedded hearing aid by using a compact microphone (e.g. MEMS microphone) and a micro-speaker. The hearing assistance system may be used to implement an active sound path versus the present passive path formed by an air channel. One of ordinary skill in the art would ordinary skill in the art would appreciate that there may be a primary sensor that could be configured with a variety of component sensors each capable of collecting different types of data, and embodiments of the present invention are contemplated for use with any suitable component sensor to expand the data collection capabilities of the primary sensor. One of ordinary skill in the art would further appreciate that the various sensors could be incorporated or embedded into any number of wearable articles that could be attached or substantially connected directly to the head, and embodiments of the present invention are contemplated for use with any such wearable articles.

Turning now to FIG. 10, a diagram of an exemplary embodiment of an inertial sensor adapted formed as an earpiece. In a preferred embodiment, the earpiece inertial sensors may be configured with components that include, but are not limited to, a sensing module, an active hearing module, and a power source such as a battery. In the preferred embodiment, the sensing module may be comprised of sub-components that include, but are not limited to, a 3-axis liner accelerometer, a 1-axis gyroscope, a sensor interface and control unit, and a wireless data and power unit. In the preferred embodiment, the sensor interface and control unit manages the sensors sampling, data formatting and the transfer of data to the wireless data and power unit. In the preferred embodiment, the wireless data and power unit may be based on a standard inductive coupling low-frequency RFID that provides both wireless data communication to the wireless data link that is in the helmet and wireless charging of the earpiece internal battery both during operation and off-line for full-recharge. In the preferred embodiment, the wireless power may provide 40%-60% of the overall system in-operation power relaxing the battery requirements and enabling 5-6 hours of operation with a small 12 mAHr battery. Alternate embodiments of the inertial sensor may be comprised of fewer or additional components than as discussed above and each component may be comprised of fewer of additional subcomponents than as discussed above. One of ordinary skill in the art would appreciate that the inertial sensor may be comprised of fewer or additional components and subcomponents without departing from the scope of the invention, and embodiments of the present invention are contemplated for use with any such component or subcomponent.

According to an embodiment of the present invention, the system may also be useful for measuring the acceleration force delivered to any rigid body. In a preferred embodiment, the inertial sensor set could be appropriately aligned on any rigid body to measure the kinematics experienced by that body. A rigid body and appropriate placement of the sensors on that rigid body, for example aligning two sensors on the appropriate axis, is important in order to provide accurate measurement of body kinematics. One example of a practical application could be to measure the impact and resultant kinematics experienced by the various limbs and appendages of an anthropomorphic test device (i.e. crash test dummy). In this example, rather than only using one inertial sensor set, multiple inertial sensor sets might be used so that the acceleration of each limb or portion thereof could be accurately measured. For example, one set of inertial sensors would be used to measure the kinematics of the upper portion of a limb (e.g. upper arm or thigh), while another set of sensors would be used to measure the kinematics of a lower portion of a limb (e.g. forearm or lower leg kinematics, as physically speaking the forearm and upper arm are two separate rigid bodies. One of ordinary skill in the art would appreciate that the system and inertial sensors could be employed on any rigid body, and embodiments of the present invention are contemplated for such rigid body.

According to an embodiment of the present invention, the system may calculate impact and acceleration data from as few as two inertial sensors. In a first preferred embodiment, the system employs two inertial sensors, such as linear accelerometers, that are retained within earpieces that are worn by a user. One version of the earpiece based system employs two earpiece sensor systems, each including a 3-axis linear accelerometer and an active hearing aid system. In the preferred embodiment of the earpiece based system, at least one of the ear sensors may also include a single-axis gyroscope (rate of rotation sensor) with large dynamic range (±20,000 deg/sec) and high bandwidth (~2 kHz). In the preferred embodiment, an algorithm such as the one discussed in the following paragraphs may be used to derive the three axis angular accelerations from the linear accelerometers and single axis gyroscope. One of ordinary skill in the art would appreciate that there numerous calculation methods and sensor arrangements that could be used to determine acceleration and impact data, and embodiments of the present invention are contemplated with for use with any such calculation method or sensor arrangement.

According to an embodiment of the present invention, acceleration and impact data may be calculated based on the data measured by two inertial sensors. In a preferred embodiment, the inertial sensors may be incorporated into earpieces. One possible example of how the coordinate system of the two earpiece sensor scheme could be implemented is illustrated in FIGS. 5A and 5B, in particular with the orientation of the x, y, and z axis as shown. As an illustrative example, the two earpiece sensor system, as shown in FIGS. 5A and 5B has one sensor in each of the left and right ears (point 1 and point 2), placing both the sensors on the same axis, which in this example is horizontal axis y. Continuing with the two earpiece sensor system, the middle point between the ears is set as the origin (point 0). In some cases, including the present example, point 0 is not necessarily the center of gravity (CG) of the rigid body that is being measured. The CG kinematics can be derived from point 0 kinematics through common translation equations if these two points are far from each other. Determining the kinematics of the origin in six degrees of freedom (DOF) allows for the kinematics of the center of gravity to be calculated.

According to an embodiment of the present invention, the body being measured is a rigid body. Continuing with the two earpiece example discussed above, the head of a person with an earpiece sensor in each of the ears represents one example of a rigid body. In the preferred embodiment a series of equations, algorithms, and other computations are utilized to produce a repeatable method of calculating the impact and acceleration data measured by six linear accelerometers and one gyroscope (e.g. three orthogonal axis linear sensors at each reference point, along with a gyroscope at one of those reference points), a preferred example of such a calculation method is detailed below.

According to a preferred embodiment of the calculation method, the kinematic relationship between point 1 (e.g. right ear) can be expressed in vector form as equation (A.1):

$$\vec{A}_1 = \vec{A}_0 + \vec{\omega} \times (\vec{\omega} \times \vec{r}_{01}) + \vec{\dot{\omega}} \times \vec{r}_{01} \qquad (A.1)$$

$\vec{A}_1$ the linear acceleration of point 1 with respect to point 0 (e.g. skull), which can be measured with three linear accelerometers at point 1, therefore $\vec{A}_1 = [A_{x1}, A_{y1}, A_{z1}]^T$; $\vec{A}_0$ is the linear acceleration of point 0, therefore $\vec{A}_0=[A_{x0},A_{y0},A_{z0}]^T$; $\vec{\omega}$ is the angular velocity of the head, therefore $\vec{\omega}=[\omega_x,\omega_y,\omega_z]^T$; $\dot{\vec{\omega}}$ is the angular acceleration of the head, therefore $\dot{\vec{\omega}}=[\dot{\omega}_x,\dot{\omega}_y,\dot{\omega}_z]^T$; $\vec{r}_{01}$ is the displacement vector between point 0 and point 1, therefore, in the scheme of the preferred calculation method, $\vec{r}_{01}=[0,r,0]^T$, where r is the distance between point 0 and 1. With a similar definition at point 2, $\vec{A}_2=[A_{x2},A_{y2},A_{z2}]^T$ and $\vec{r}_{02}=[0,-r,0]^T$ in the scheme preferred calculation, the vector form expression of the kinematic relationship of point 0 and point 2 as the following equation (A.2):

$$\vec{A}_2=\vec{A}_0+\vec{\omega}\times(\vec{\omega}\times\vec{r}_{02})+\dot{\vec{\omega}}\times\vec{r}_{02} \quad (A.2)$$

Therefore, equation (A.1) can be expressed in the following matrix form:

$$\begin{bmatrix}A_{x1}\\A_{y1}\\A_{z1}\end{bmatrix}=\begin{bmatrix}A_{x0}\\A_{y0}\\A_{z0}\end{bmatrix}+\begin{bmatrix}\omega_x\\\omega_y\\\omega_z\end{bmatrix}\times\left(\begin{bmatrix}\omega_x\\\omega_y\\\omega_z\end{bmatrix}\times\begin{bmatrix}0\\r\\0\end{bmatrix}\right)+\begin{bmatrix}\dot{\omega}_x\\\dot{\omega}_y\\\dot{\omega}_z\end{bmatrix}\times\begin{bmatrix}0\\r\\0\end{bmatrix} \quad (A.3)$$

Consequently, three equations can be derived from the matrix of (A.3)

$$A_{x1}=A_{x0}+\omega_x\omega_y r-\dot{\omega}_z r \quad (A.4)$$

$$A_{y1}=A_{y0}-(\omega_x^2+\omega_z^2)r \quad (A.5)$$

$$A_{z1}=A_{z0}+\omega_y\omega_z r+\dot{\omega}_x r \quad (A.6)$$

An analogous set of three equations can be derived for point 2:

$$A_{x2}=A_{x0}-\omega_x\omega_y r+\dot{\omega}_z r \quad (A.7)$$

$$A_{y2}=A_{y0}+(\omega_x^2+\omega_z^2)r \quad (A.8)$$

$$A_{z2}=A_{z0}-\omega_y\omega_z r-\dot{\omega}_x r \quad (A.9)$$

With addition of equations (A.4)+(A.7), (A.5)+(A.8) and (A.6)+(A.9), the result is:

$$A_{x0}=(A_{x1}+A_{x2})/2 \quad (A.10)$$

$$A_{y0}=(A_{y1}+A_{y2})/2 \quad (A.11)$$

$$A_{z0}=(A_{z1}+A_{z2})/2 \quad (A.12)$$

From equations (A.10) through (A.12), the three-axis linear accelerations of the origin can be calculated with the linear accelerations measured in the six linear accelerometers installed in the two earpieces sensors. Further, with subtraction of equations (A.7)−(A.4), (A.8)−(A.5) and (A.6)−(A.9), the result is:

$$\dot{\omega}_z=(A_{x2}-A_{x1})/2r+\omega_x\omega_y \quad (A.13)$$

$$\omega_x^2+\omega_z^2=(A_{y2}-A_{y1})/2r \quad (A.14)$$

$$\dot{\omega}_x=(A_{z1}-A_{z2})/2r-\omega_y\omega_z \quad (A.15)$$

From equations (A.13)-(A.15), the calculation scheme is not able to mathematically calculate the angular acceleration on y-axis, $\dot{\omega}_y$, but the other two angular accelerations can be numerically solved with integration. By adding an additional out-of-plane gyroscope (sensing axis is out of plane) that is aligning its sensing axis to y-axis to measure $\omega_y$, the angular acceleration of all three axes can be numerically solved with initial conditions.

Figure 9:
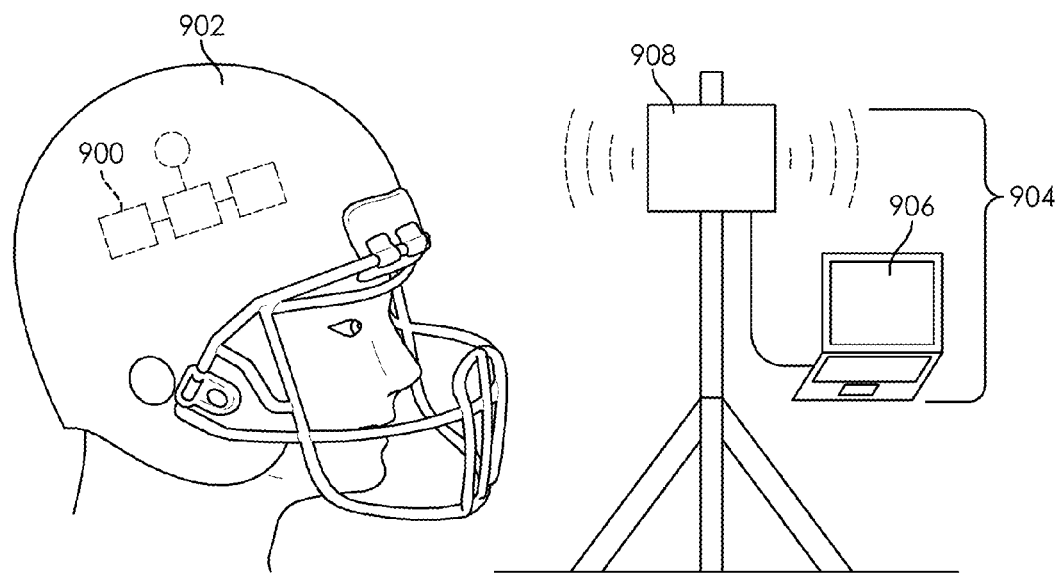
FIG. 9 is an illustration of a remote recording station in wireless communication with a wireless data link unit mounted in a helmet in accordance with an embodiment of the present invention.

According to an alternate preferred embodiment of the present invention, the two earpiece sensor system can be extended to include an additional reference or sensor point. In the preferred embodiment, a third point (point 3) may be established at the top of head to directly align to origin (point 0) on the z axis as illustrated in FIG. 9. The kinetic definitions of point 3 are similarly $\vec{A}_3=[A_{x3},A_{y3},A_{z3}]^T$ and $\vec{r}_{03}=[0,0,-r_{03}]^T$, where $r_{03}$ is the distance between point 0 and 3. With the additional reference point, a similar equation set in matrix form can be derived as follows:

$$\begin{bmatrix}A_{x3}\\A_{y3}\\A_{z3}\end{bmatrix}=\begin{bmatrix}A_{x0}\\A_{y0}\\A_{z0}\end{bmatrix}+\begin{bmatrix}\omega_x\\\omega_y\\\omega_z\end{bmatrix}\times\left(\begin{bmatrix}\omega_x\\\omega_y\\\omega_z\end{bmatrix}\times\begin{bmatrix}0\\0\\-r_{03}\end{bmatrix}\right)+\begin{bmatrix}\dot{\omega}_x\\\dot{\omega}_y\\\dot{\omega}_z\end{bmatrix}\times\begin{bmatrix}0\\0\\-r_{03}\end{bmatrix} \quad (A.16)$$

From A.3, the following three equations can be derived:

$$A_{x3}=A_{x0}-\omega_x\omega_z r_{03}-\dot{\omega}_y r_{03} \quad (A.17)$$

$$A_{y3}=A_{y0}-\omega_y\omega_z r_{03}+\dot{\omega}_x r_{03} \quad (A.18)$$

$$A_{z3}=A_{z0}+(\omega_x^2+\omega_y^2)r_{03} \quad (A.19)$$

From (A.9) and (A.18), the following equation is derived:

$$\dot{\omega}_x=(A_{y3}-A_{y0})/2r_{03}-(A_{z2}-A_{z0})/2r \quad (A.20)$$

Therefore, $\dot{\omega}_x$ can be also algebraically calculated by adding one more linear accelerometer at point 3 to measure y-axis acceleration. It is worthwhile to note that point 3 can be any point on the z axis. Furthermore, the third inertial sensor could be installed, for example, in a mouth guard, so long as the sensor is on z axis. From equation A.15, $\omega_z$ can be calculated as follows:

$$\omega_z(A_{z0}-A_{z2})/r\omega_y-\dot{\omega}_x/\omega_y \quad (A.21)$$

It is also important to note that, when deriving the kinematic parameters, integration steps should be generally avoided since it will require initial conditions to solve the differential equation. On the other hand, calculating acceleration with a derivative step is more accurate numerically since it only it involves only two steps that are next to each other in time domain. For example, since $\omega_y$ can be measured, it is accurate to numerically calculate $\dot{\omega}_y$. With $\dot{\omega}_y$ known, $\omega_x$ can be calculated via equation A.17:

$$\omega_x=(A_{x0}-A_{x3})/r_{03}\omega_z-\dot{\omega}_y/\omega_z \quad (A.22)$$

Finally, $\dot{\omega}_z$ can also algebraically be solved from equation A.13. Therefore, by introducing two linear accelerometers at point 3 in the x and y directions (z direction accelerometer at point 3 is not needed), $\dot{\omega}_x,\dot{\omega}_y,\dot{\omega}_z$ can be derived without any integration and only one derivative step of $\omega_y$.

Figure 7:
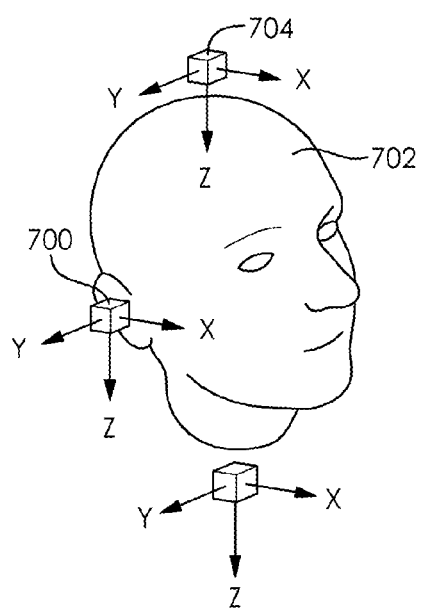
FIG. 7 is a right side view of a coordinate system for a three inertial sensor system attached to a head in accordance with an embodiment of the present invention.
Figure 8:
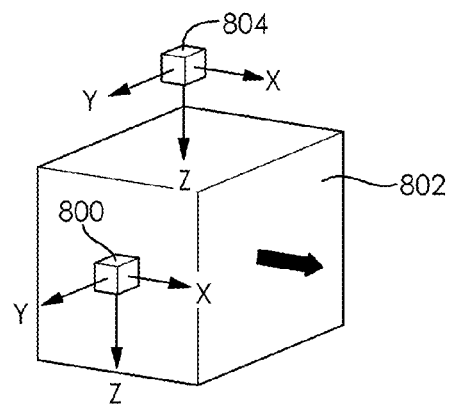
FIG. 8 is a right side view of a coordinate system of a three inertial sensor system attached to a rigid body in accordance with an embodiment of the present invention.

In the preferred embodiment, the three reference point calculation method would improve the accuracy from a two earpiece system, since most acceleration parameters are algebraically solved. As previously discussed, the location of the third inertial sensor set should be on the z-axis as shown in FIGS. 7 and 8. If the third sensor is on the top of head, it may present coupling issues due to hair between the sensor and the skull of the user. As a solution to this issue, a potential location is to install the third sensor in a mouth guard. The use of a mouth guard based sensor presents its own limitations with coupling, as a mouth guard can be knocked out of the mouth or otherwise become loose within the mouth. Therefore, the preferred embodiment of the present invention incorporates solutions to account for those times when the third inertial sensor set (e.g. mouth guard) is not tightly coupled to the head. For example, in embodiments of the present invention that use a mouth guard based sensor, it is possible to develop a hybrid system to utilize the measurement when from the mouth guard when the mouth guard is firmly coupled to the head. When the mouth guard is loose, the system can change back to the two earpiece system and calculate the kinematics through the two-reference point calculation method. One of ordinary skill in the art would appreciate that there are many methods for determining whether to include the data from a third inertial sensor set based on the coupling of that third inertial sensor set, and embodiments of the present invention are contemplated for use with any such method.

According to an embodiment of the present invention, the system may employ a calculation method that uses a 6-DOF acceleration solution. The angular velocity $\omega_x, \omega_y, \omega_z$ and angular acceleration $\dot{\omega}_x, \dot{\omega}_y, \dot{\omega}_z$ cannot be algebraically calculated from the eqs. (A.13)-(A.15). Further, $\dot{\omega}_y$ is not presented in these equations and therefore cannot be calculated. Therefore, in the most preferred embodiment the number of sensors sets may be reduced to only being attached at a first reference point and second reference point by adding a single-axis gyroscope at one of the reference points (for example, at the first reference point) to measure the $\omega_y$, and subsequently $\dot{\omega}_y$ can be numerically calculated by derivative of $\omega_y$. Importantly, the addition of a gyroscope at one of the reference points allows the system accurately measure kinematic of a rigid body using only two reference points. With $\omega_y$ known, equations (A.13) and (A.15), can be numerically solved providing initial conditions of $\omega_x, \omega_z$ and $\dot{\omega}_x, \dot{\omega}_z$. Typically, these initial conditions are conveniently set to zero when the system initializes. It is commonly believed that the accuracy of the numerical solution of these two differential equations can result in accumulated errors over time due to integration steps. However, as will be detailed in the following section, at the beginning of each impact, by assuming the initial conditions $\omega_x, \omega_z$ being zero (which is an accurate assumption without impact) and resetting the initial conditions of $\omega_x, \omega_z$ to zero (which can either be triggered with an impact event or by the system), the integration will be reduced to tens of milliseconds. As a result, the numerical solution of $\dot{\omega}_x, \dot{\omega}_z$ is accurate in a large measured range. Hence, the two earpiece system which contains six linear accelerometers and one single-axis gyroscope in the y-axis direction can accurately measure the kinematics of a rigid body (e.g. the head) in 6-DOF.

The calculation methods discussed above are provided by way of example are not to be construed in any way as to limit the scope of the invention. One of ordinary skill in the art would appreciate that there are numerous alternative calculation methods that could be used without departing from the spirit and scope of the invention described herein, and embodiments of the present invention are contemplated for use with any such alternative calculation method.

Figure 1:
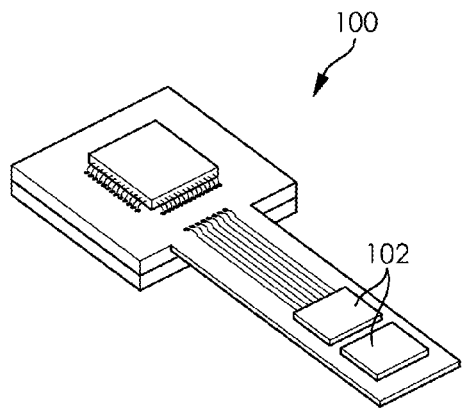
FIG. 1 is a perspective view of an inertial sensor set in accordance with an embodiment of the present invention.
Figure 2:
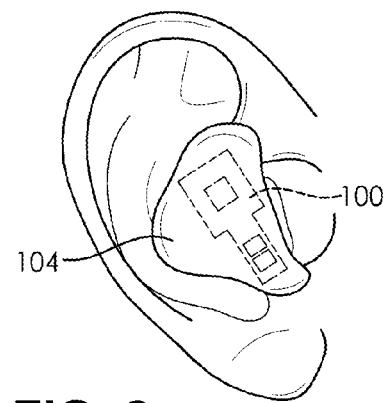
FIG. 2 is an illustration of an inertial sensor set formed as an earpiece in accordance with an embodiment of the present invention.
Figure 3:
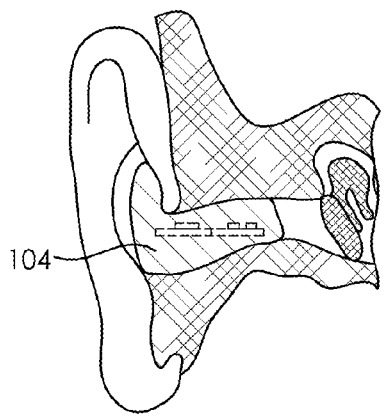
FIG. 3 is a is a cross-sectional view of an inertial sensor set formed as an earpiece positioned inside of an ear in accordance with an embodiment of the present invention.
Figure 4:
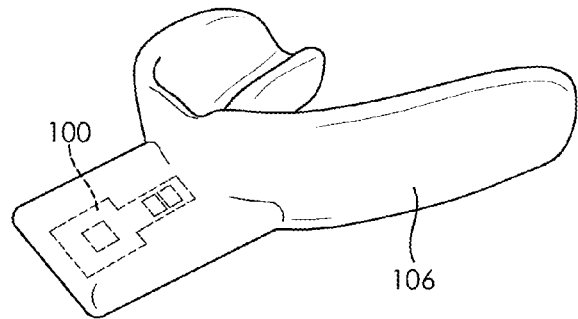
FIG. 4 is an illustration of an inertial sensor set formed as a mouth guard in accordance with an embodiment of the present invention.

Turning now to FIGS. 1-4, exemplary form factors for an inertial sensor set in accordance with embodiments of the present invention. As shown in FIG. 1, an inertial sensor set 100 is primarily comprised of an assortment of inertial sensors 102, including but not limited to, accelerometers and gyroscopes. As illustrated by FIGS. 2 and 3, the inertial sensor set 100 may be formed as or embedded inside of an earpiece 104, which would allow the inertial sensor to be firmly connected to the head of a user. As illustrated by FIG. 4, the inertial sensor set 100 may be formed as or embedded inside of a mouth guard 106. In a preferred embodiment, a mouth guard 106 mounted inertial sensor set 100 pairing with two inertial sensor sets 100 that are mounted in two ears, could provide more accuracy of kinematic calculation of the origin point.

Turning now to FIGS. 5A and 5B, a coordinate system showing an exemplary arrangement of two inertial sensor sets on the head of a person 502. In a preferred embodiment, the acceleration measurement system employs a first inertial sensor set attached at a first reference point 500 and a second inertial sensor set attached at a second reference point 501 to collect acceleration data. In the preferred embodiment, the inertial sensor sets may be attached to each ear on the head of a person. To collect more accurate measurements, it is preferred that the first reference point 500 aligns with the second reference point 501 on a common axis as shown in FIGS. 5A and 5B.

Turning now to FIGS. 6A and 6B, a coordinate system showing an exemplary arrangement of two inertial sensors sets on a rigid body 602. In a preferred embodiment, the acceleration measurement system employs a first inertial sensor set attached at a first reference point 600 and a second inertial sensor set attached at a second reference point 601 to collect acceleration data. In the preferred embodiment, the inertial sensor sets are attached to the rigid body 602 where the first reference point 600 aligns with the second reference point 601 on a common axis as shown in FIGS. 6A and 6B. Aligning the inertial sensor sets on a common axis provides for a more accurate collection of acceleration data.

Turning now to FIG. 7, a coordinate system showing an exemplary arrangement of three inertial sensor sets on the head of a person 702. In an alternate preferred embodiment, the acceleration system may employ three sets of inertial sensors mounted at three different reference points to collect acceleration data. In the preferred embodiment, the first and second sets of inertial sensors 700 are aligned on a common axis, such as the y axis, while the third set of inertial sensors 704 is on a perpendicular axis and out-of-plane with the first and second inertial sensor sets 700, such as on top of the head 702 or in a mouth guard. In a preferred embodiment, the perpendicular axis typically intersects with an origin point that exists substantially equidistant from both the first and second inertial sensors sets 700.

Turning now to FIG. 8, a coordinate system showing an exemplary arrangement of three inertial sensor sets on a rigid body. In an alternate preferred embodiment, the acceleration system may employ three sets of inertial sensors mounted at three different reference points to collect acceleration data. In the preferred embodiment, the first and second sets of inertial sensors 800 are aligned on a common axis while the third inertial sensor set 804 is aligned on a perpendicular axis and out-of-plane with the first and second inertial sensors sets 804. In a preferred embodiment, the perpendicular axis typically intersects with an origin point that exists substantially equidistant from both the first and second inertial sensors sets 800

Turning now to FIG. 9, an illustrative example of a remote recording station in wireless communication with a wireless data link unit mounted in a helmet in accordance with an embodiment of the present invention. In a preferred embodiment, a wireless data link unit 902 may be mounted in the helmet of a person that has a plurality of inertial sensor sets attached to their head or the helmet 900 the person is wearing. In the preferred embodiment, the wireless data link unit 902 may receive data from the plurality of inertial sensor sets and then transmit that data to a remote recording station 904. The remote recording station 904 could then perform an analysis on the data obtained from the plurality of inertial sensor sets in order to calculate acceleration information. The link between created by the wireless data link unit 902 may be either a one-way or two-way link between the plurality of the inertial sensor sets and the remote recording station 904 as needed based on a particular application. In the preferred embodiment, the remote recording station may primarily consist of a computing device 906 with a means for receiving and transmitting information 908 to the wireless data link unit 902 and the plurality of inertial sensor sets.

Turning now to FIG. 10, schematic of an exemplary embodiment of an inertial sensor set 1000 formed as wireless earpiece sensor in accordance with an embodiment of the present invention. In a preferred embodiment, the earpiece inertial sensor 1000 is primarily comprised of a sensor interface and control unit 1002, a 3-axis linear accelerometer 1004, a 1-axis gyroscope 1006, a temperature sensor 1008, a speaker 1010, an amplifier 1012, a microphone 1014, a power source 1016, and a wireless data and power manager 1018. One of ordinary skill in the art would appreciate that the wireless earpiece sensor could include additional, fewer, or functionally components and embodiments of the present invention are contemplated for use with any such component.

Figure 11:
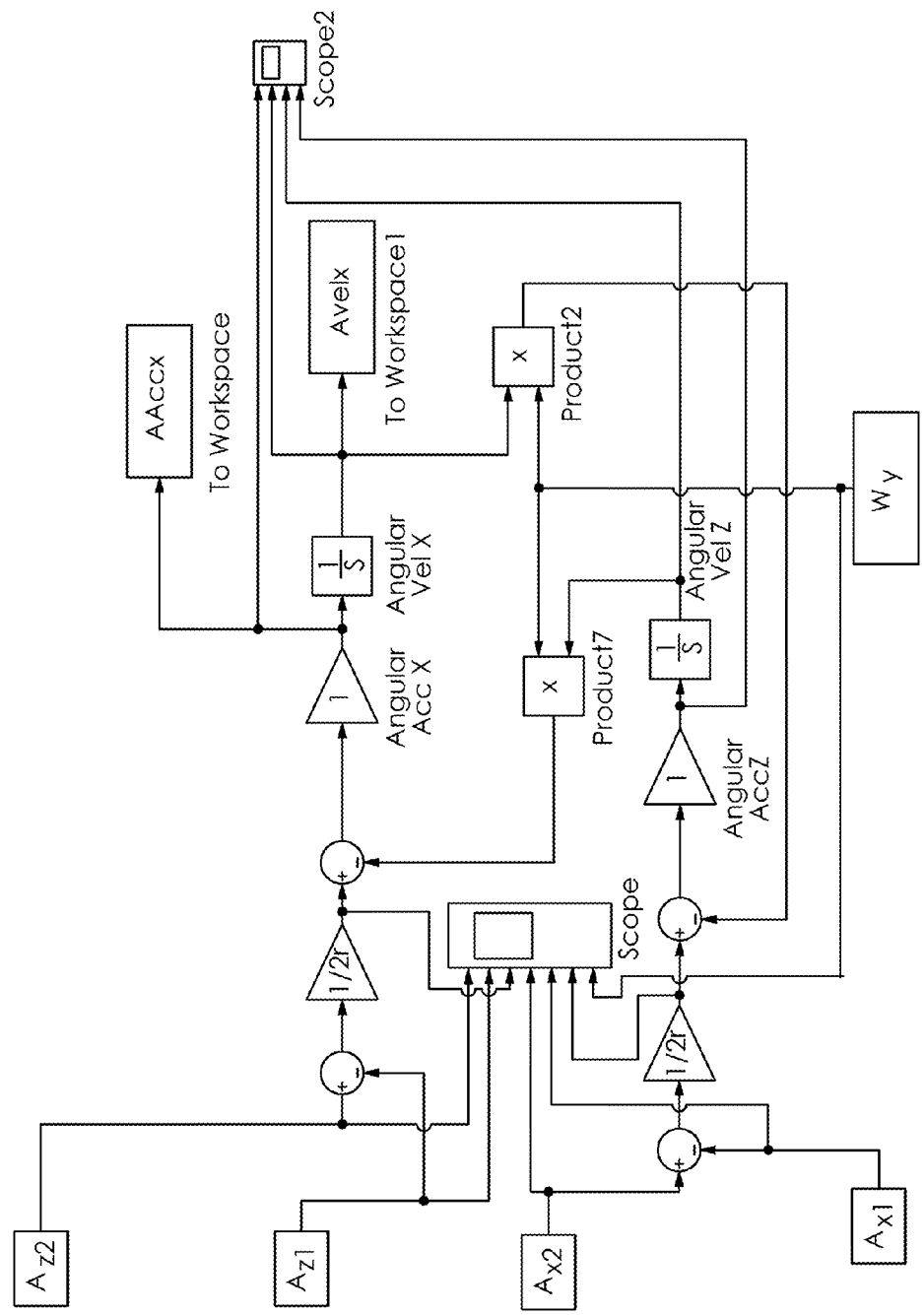
FIG. 11 is a schematic diagram of an exemplary numerical model employed by the system in accordance with an embodiment of the present invention.

Turning now to FIG. 11, a graphical representation of a numerical model to solve $\omega_x, \omega_z$ with different initial conditions and five sensor measurements (i.e. measurement of $A_{x1}, A_{x2}, A_{z1}, A_{z2}, \omega_y$). In this model, each sensor measurement is emulated with a finite impulse acceleration response (velocity response in $\omega_y$ case) of a $2^{nd}$ order dynamic system with different damping and stiffness.

Turning now to FIGS. 12-14, schematic overviews of various embodiments of a head acceleration measurement system. As shown in FIG. 12, some embodiments of the system may only use head attached inertial sensors for collecting acceleration data, while in other embodiments, as shown in FIGS. 13 and 14, the system may employ both head and helmet attached inertial sensors. For example, as shown in FIG. 12, the system 1200 may only use inertial sensors that are attached to the head 1202, while the in-helmet mounted electronics 1204 are configured without any inertial sensors. However, in other embodiments, as shown in FIG. 13, the system 1300 may use inertial sensors that are attached to both the head 1302 and that are included within the in-helmet mounted electronics 1304. Additionally, as shown in FIG. 14, the system 1400 may also include in-helmet mounted electronics 1404 that incorporate physiological sensors. In the any of the preferred embodiment, data will be collected and measured by one or more inertial sensor sets and transmitted to a remote recording system on a sideline via a helmet mounted sensor set or wireless data link unit.

Turning now to FIG. 15, an exemplary method flow for processing acceleration data and calculating the kinematics of an impact. In a preferred embodiment, the method begins at step 1500 with a plurality of inertial sensor sets outputting acceleration data to a processing unit. Next, at step 1502, the processing unit calculates the acceleration and other kinematic information based on the data received from the inertial sensor sets. In a preferred embodiment, at step 1504, a series of algorithms and equations are relied upon to process the acceleration data.

Turning now to FIG. 16, an exemplary method flow for processing acceleration data and calculating the kinematics of an impact when acceleration data is received from multiple sources. In a preferred embodiment, the method begins at steps 1600 and 1602 with acceleration data being collected from various sources. Next, at step 1604, the acceleration data from the various sources is processed and compared in order to provide more accurate results regarding the acceleration and related kinematic information. In a preferred embodiment, at step 1606, a series of algorithms and equations are relied upon to process and compare the acceleration data from the various sources.

It should be noted that the features illustrated in the drawings are not necessarily drawn to scale, and features of one embodiment may be employed with other embodiments as the skilled artisan would recognize, even if not explicitly stated herein. Descriptions of well-known components may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. A system for determining the acceleration delivered to an object as a result of an impact, the system comprising:
   a plurality of sensor modules configured to detect an acceleration force applied to a user's head,
      wherein at least one of said sensor modules is embedded in an earpiece worn inside in car of the user, and another of said sensor modules is mounted in a helmet worn by the user,
      wherein each sensor module comprises a 3-axis linear accelerometer, a sensor interface and control unit, and a wireless data and power unit,
      wherein at least one of said sensor modules includes a gyroscope;
   a wireless data link mounted inside the helmet;
   an acceleration data processing module comprising computer-executable code stored in non-volatile memory;
   a processor;
   a memory; and
   a communications means,
   wherein said acceleration data processing module, said processor, said memory, and said communications means are operably connected and are configured to:
   receive acceleration data from said plurality of sensors via said wireless data link; and
   analyze said acceleration data collected by said sensor modules
   wherein sensor data from the earpiece sensor module is used to correct for inaccuracies in sensor data from the helmet sensor module caused by the helmet moving independently of the user's head in response to an impact.

2. The system of claim 1, wherein said acceleration data processing module, said processor, said memory, and said communications means are operably connected and are configured to:
   identify when said acceleration value exceeds a preset threshold; and
   send an alert notification when said acceleration value exceeds said preset threshold.

3. A method for determining the acceleration delivered to an object as a result of an impact force, the method comprising the steps of:
   detecting an acceleration force being applied to a user's head with a plurality of sensor modules configured to detect the acceleration force, wherein at least one of said sensor modules is embedded in an earpiece worn inside an ear of the user, and another of said sensor modules is mounted in a helmet worn by the user, wherein each sensor module comprises a 3-axis linear accelerometer, a sensor interface and control unit, and a wireless data and power unit, wherein at least one of the said sensor modules includes a gyroscope;

transmitting acceleration data from said sensors, via a wireless data link mounted in said helmet, to data processing module for analysis; and analyzing said acceleration data collected by said sensor modules at said data processing module wherein sensor data from the earpiece sensor module is used to compensate for inaccuracies in sensor data from the helmet sensor module caused by the helmet moving independently of the user's head in response to an impact.

4. The method of claim 3, further comprising the steps of: transmitting said acceleration data to a remote recording station.

5. The system of claim 1, wherein a second sensor module of said plurality of sensor modules is embedded in a second earpiece worn in another ear of the user.

6. The system of claim 1, wherein the first and second sensor modules are positioned along a horizontal axis that extends through the first and second sensor modules embedded in their respective earpieces.

7. The system of claim 1, wherein the wireless data and power unit utilizes a standard inductive coupling low-frequency RFID that provides both wireless data communication to the wireless data link and wireless charging of a battery that powers components of the earpiece.

8. The system of claim 1, wherein the earpiece sensor module output is used to compensate for imperfections in the coupling between the helmet and head of a user.

9. The system of claim 1, wherein an alert is transmitted when an impact or acceleration threshold is exceeded.

10. The system of claim 1, wherein an alert is transmitted when an impact or acceleration threshold is exceeded.

11. A system for determining the acceleration delivered to an object as a result of an impact, the system comprising:

a sensor module embedded in an earpiece worn inside an ear of a user, said sensor module includes a 3-axis orthogonal linear accelerometer, a sensor interface and control unit, a wireless data and power unit, and a gyroscope that measures rotation about an axis perpendicular to the user's ear;

a sensor module and a wireless data link mounted inside the helmet:

an acceleration data processing module comprising computer-executable code stored in non-volatile memory;

a processor;

a memory; and a communications means, wherein said acceleration data processing module, said processor, said memory, and said communications means are operably connected and are configured to:

receive data from said sensor module via said wireless data link; and analyze said acceleration data collected by said sensor module to determine a displacement of the head's center of gravity, its velocity, and its acceleration after impact.

12. The system of claim 11, wherein said earpiece includes a micro-speaker.

13. The system of claim 11, wherein said earpiece includes a microphone.

14. The system of claim 11, wherein a third sensor is embedded in a mouth guard of the user.

15. The system of claim 11, wherein said third sensor is disposed along a vertical axis that intersects a point substantially equidistant from said first and second sensors.

16. The system of claim 11, wherein a third sensor is embedded in a helmet worn by the user.

17. The system of claim 11, wherein each of said first and second earpiece sensors comprise a temperature sensor, a speaker, an amplifier, a microphone, a power source, and a wireless data and power manager.

18. The system of claim 11, wherein said acceleration data processing module computes rotation kinematics based on rotation data acquired from the gyroscope about an axis that passes through an ear of the user, and uses the rotation data to determine rotation kinematics of the center of gravity of the user's head in three orthogonal axes.

* * * * *